US007377946B2

(12) United States Patent
Gourlaouen et al.

(10) Patent No.: US 7,377,946 B2
(45) Date of Patent: May 27, 2008

(54) COMPOSITION COMPRISING AT LEAST ONE SUBSTITUTED 2-[2-(4-AMINO PHENYL)ETHENYL]-1-PYRIDINIUM DERIVATIVE, PROCESS FOR TREATING KERATIN FIBRES USING IT, DEVICE AND USE THEREOF

(75) Inventors: Luc Gourlaouen, Asnieres (FR); Andrew Greaves, Montevrain (FR); Grégory Plos, Tokyo (JP)

(73) Assignee: L'Oréal, Paris (FR)

( * ) Notice: Subject to any disclaimer, the term of this patent is extended or adjusted under 35 U.S.C. 154(b) by 462 days.

(21) Appl. No.: 10/885,888

(22) Filed: Jul. 8, 2004

(65) Prior Publication Data

US 2005/0191253 A1 Sep. 1, 2005

Related U.S. Application Data

(60) Provisional application No. 60/488,805, filed on Jul. 22, 2003.

(30) Foreign Application Priority Data

Jul. 9, 2003 (FR) .................................. 03 08398

(51) Int. Cl.
*A61K 7/13* (2006.01)
(52) U.S. Cl. ..................... 8/405; 8/406; 8/407; 8/409; 8/410; 8/411; 8/421; 8/435; 8/648
(58) Field of Classification Search ............... 8/405, 8/406, 407, 409, 410, 411, 421, 435, 648
See application file for complete search history.

(56) References Cited

U.S. PATENT DOCUMENTS

| 2,528,378 | A | 10/1950 | McCabe, Jr. et al. |
| 2,781,354 | A | 2/1957 | McCabe, Jr. et al. |
| 2,798,053 | A | 7/1957 | Brown |
| 2,923,692 | A | 2/1960 | Ackerman et al. |
| 3,915,921 | A | 10/1975 | Schlatzer |
| 4,237,243 | A | 12/1980 | Quack et al. |
| 4,509,949 | A | 4/1985 | Huang et al. |
| 4,608,379 | A | 8/1986 | Boyle |
| 4,823,985 | A | 4/1989 | Grollier et al. |
| 4,997,745 | A | 3/1991 | Kawamura et al. |
| 5,089,578 | A | 2/1992 | Valint et al. |
| 5,708,151 | A | 1/1998 | Möckli |
| 5,792,221 | A | 8/1998 | Lagrange et al. |
| 5,914,373 | A | 6/1999 | Glancy et al. |
| 6,120,780 | A | 9/2000 | Dupuis et al. |
| 6,770,102 | B1 | 8/2004 | Moeller et al. |
| 6,822,039 | B1 | 11/2004 | Monfreux-Gaillard et al. |
| 2003/0124079 | A1 | 7/2003 | Mougin et al. |
| 2004/0205901 | A1 | 10/2004 | Cottard et al. |
| 2005/0028301 | A1 | 2/2005 | Pastore |

FOREIGN PATENT DOCUMENTS

| DE | 199 36 911 A1 | 2/2001 |
| EP | 0 173 109 | 10/1989 |
| EP | 0 395 282 | 10/1990 |
| EP | 0 503 853 | 9/1992 |
| EP | 0 714 954 | 6/1995 |
| EP | 0 750 899 | 1/1997 |
| EP | 0 815 828 | 1/1998 |
| FR | 2 416 723 | 10/1979 |
| FR | 2 586 913 | 3/1987 |
| FR | 2 692 572 | 12/1993 |
| FR | 2 811 993 | 1/2002 |
| FR | 2 820 032 | 8/2002 |
| FR | 2 830 189 A1 | 4/2003 |
| WO | WO 95/01772 | 1/1995 |
| WO | WO 95/15144 | 6/1995 |
| WO | WO 00/31154 | 6/2000 |
| WO | WO 00/68282 | 11/2000 |

OTHER PUBLICATIONS

Indian Journal of Technology, dated 1989.*
STIC Search Report dated Apr. 10, 2007.*
French Search Report for FR 03 08398, dated Mar. 17, 2004.
Database CA 'en lignel, Chemical Abstracts Service, Columbus, Ohio, US; Sahay, A.K. et al, "Solubilization of Surface-Active Cyanine Dyes in Cetyltrimethyl Ammonium Bromide (CTAB) Solution Through Mixed Micelle Formation," Indian Journal of Technology, vol. 27, No. 2, 1989, pp. 89-92.
Fonnum et al., "Associative Thickeners. Part I: Synthesis, Rheology and Aggregation Behavior," Colloid Poly. Sci., vol. 271, 1993, pp. 380-389.
Morishima, Yotaro, "Self-Assembling Amphiphilic Polyelectrolytes and Their Nanostructures," Chinese Journal of Polymer Science, vol. 18, No. 40, 2000, pp. 323-336.
Noda et al., "Micelle Formation of Random Copolymers of Sodium 2-(Acrylamido)-2-methylpropanesulfonate and a Nonionic Surfactant Macromonomer in Water As Studied by Fluorescence and Dynamic Light Scattering," Macromolecules, vol. 33, No. 10, 2000, pp. 3694-3704.

(Continued)

*Primary Examiner*—Eisa Elhilo
(74) *Attorney, Agent, or Firm*—Finnegan, Henderson, Farabow, Garrett & Dunner, LLP

(57) ABSTRACT

The invention relates to a composition comprising, in a cosmetically acceptable medium, at least one particular fluorescent dye.

The invention also relates to a process for treating keratin fibres, in particular human keratin fibres, using this composition, and also to a device comprising it.

Finally, the invention relates to the use of the composition according to the invention as a lightening agent or as a colouring agent for the said fibres.

42 Claims, No Drawings

OTHER PUBLICATIONS

Noda et al., "Solution Properties of Micelle Networks Formed by Nonionic Surfactant Moieties Covalently Bound to a Polyelectrolyte: Salt Effects on Rheological Behavior," Langmuir, vol. 16, No. 12, 2000, pp. 5324-5332.

Noda et al., "Stimuli-Responsive Amphiphilic Copolymers of Sodium 2-(acrylamido)-2-Methylpropanesulfonate and Associate Macromonomers," Polymer Preprints, vol. 40 No. 2, 1999, pp. 220-221.

Porter, M.R., "Nonionics," Handbook of Surfactants, Chapter 7, 1991, pp. 116-178.

Porter, M.R., "Nonionics," Handbook of Surfactants, $2^{nd}$ ed., Chapter 7, 1994, pp. 169-247.

Zviak, Charles, "Sciences des Traitements Capillaries", "Hair Treatment Sciences", Masson, 1988, pp. 215, 278.

* cited by examiner

COMPOSITION COMPRISING AT LEAST ONE SUBSTITUTED 2-[2-(4-AMINO PHENYL)ETHENYL]-1-PYRIDINIUM DERIVATIVE, PROCESS FOR TREATING KERATIN FIBRES USING IT, DEVICE AND USE THEREOF

This application claims the benefit of U.S. Provisional Application No. 60/488,805, filed Jul. 22, 2003.

FIELD OF THE INVENTION

The invention relates to a composition comprising, in a cosmetically acceptable medium, at least one particular fluorescent dye. The invention also relates to a process for treating keratin fibres using this composition, and also to a device comprising it. Finally, the invention relates to the use of the composition according to the invention as a lightening agent or as a colouring agent for the said fibres.

The present invention relates to the field of dyeing keratin fibres and more particularly dyeing the hair.

BACKGROUND OF THE INVENTION

There are essentially two types of dyeing.

The first is semi-permanent dyeing or direct dyeing, which involves dyes capable of giving the hair's natural colour a more or less pronounced change.

The dyes used are coloured and colouring substances that have a certain affinity for keratin fibres.

It should be noted that this type of dyeing fades out after several washes, which may be an inconvenience.

When it is desired to obtain a coloration that is lighter than the original colour of the fibres, it is necessary to use, with the direct dyes, at least one oxidizing agent, under alkaline pH conditions.

However, these conditions of use are not free of consequences on the properties of the treated fibres. Specifically, in the long run, the fibres are more or less degraded and have a tendency to become coarse, dull, brittle and difficult to style.

The second is permanent dyeing or oxidation dyeing. This is performed with oxidation dye precursors, which are colourless or weakly coloured compounds, comprising at least one oxidation base optionally combined with one or more couplers. Once mixed with oxidizing products, at the time of use, the precursors may give rise to coloured compounds and dyes via a process of oxidative condensation.

Given the necessary presence of an oxidizing agent in this type of dyeing, the drawbacks mentioned above also occur in this case.

It has recently been found that compositions comprising at least one fluorescent compound represent an advantageous alternative to standard processes using an oxidizing agent. Thus, for dark hair, more particularly hair with a tone height of less than or equal to 6 (dark blond), preferably less than or equal to 4 (chestnut-brown), it can be seen that there are regions for which the curve of reflectance as a function of the wavelength (between 500 and 700 nm) of hair treated with the composition comprising the fluorescent compound is higher than the curve corresponding to untreated hair. Consequently, the hair appears lighter, without it being necessary to use an oxidizing agent.

It is recalled that the notion of "tone" is based on the classification of the natural shades, one tone separating each shade from the shade immediately following or preceding it. This definition and the classification of the natural shades are well known to hairstyling professionals and are published in the book "Sciences des traitements capillaires [Hair treatment sciences]" by Charles Zviak, 1988, published by Masson, pp. 215 and 278. The tone heights range from 1 (black) to 10 (light light blond), one unit corresponding to one tone; the higher the figure, the lighter the shade.

Although such compositions constitute an advance in this field, it nevertheless remains that the stability on storage of these compositions has room for improvement.

Moreover, it would also be advantageous to further increase the wash-fastness and shampoo-fastness of the colorations obtained using these compositions.

SUMMARY OF THE INVENTION

It has been found, entirely unexpectedly, that compositions comprising at least one particular fluorescent compound make it possible to improve the stability of the said composition while at the same time observing even more satisfactory dyeing results.

A first subject of the present invention is thus a composition comprising, in a cosmetically acceptable medium, at least one fluorescent dye that is soluble in the medium, of formula (I) below:

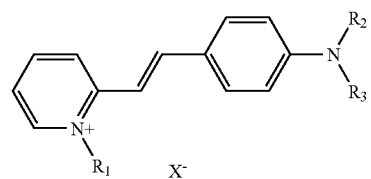

in which:

$R_1$ is a linear or branched alkyl or a cycloalkyl radical, containing 6 to 22 carbon atoms, more particularly 6 to 16 carbon atoms and preferably 8 to 12 carbon atoms, optionally substituted with at least one hydroxyl group, with at least one linear or branched $C_1$-$C_6$ alkoxy or $C_1$-$C_6$ cycloalkoxy group, and/or with at least one cyano group;

$R_2$ and $R_3$, independently of each other, represent a hydrogen atom; a linear or branched alkyl radical containing 1 to 22 carbon atoms, more particularly 1 to 10 and preferably from 1 to 6 carbon atoms, optionally substituted with one or more hydroxyl radicals;

X represents an organic or mineral anion.

A subject of the invention is similarly a process for treating keratin fibres, more particularly human keratin fibres, in which the composition according to the invention is applied to the said wet or dry fibres, for a time that is sufficient to develop the coloration, after which the fibres are rinsed, optionally washed with shampoo, rinsed again and dried, or the resulting fibres are left to dry.

According to one variant of the process, the composition according to the invention is applied to the said wet or dry fibres, without final rinsing.

Another subject of the invention consists of a device comprising the composition according to the invention.

Finally, the invention relates to the use of the composition according to the invention as an agent for lightening keratin fibres and/or as an agent for dyeing these fibres.

However, other characteristics and advantages of the invention will emerge more clearly on reading the description and the examples that follow.

In the text hereinbelow, and unless otherwise indicated, the limits of a range of values are understood as forming part of that range.

The composition according to the invention makes it possible to obtain colorations that are lighter than the original colour of the keratin fibres, when it is applied onto dark fibres, without the presence of an oxidizing agent being necessary. Needless to say, however, it is not excluded for the composition according to the invention to comprise such an agent.

According to the present invention, the term "human keratin fibres" means the hair, the eyelashes and the eyebrows.

It should be noted that the composition is suitable for treating keratin fibres, irrespective of their coloration before treatment and whether or not this coloration is natural or artificially obtained.

According to one advantageous embodiment of the invention, the composition is intended to be applied to dark keratin fibres. More particularly, the dark keratin fibres are pigmented or artificially dyed fibres, the tone height of which is less than or equal to 6 and preferably less than or equal to 4.

As indicated previously, the fluorescent dye is of formula (I) below:

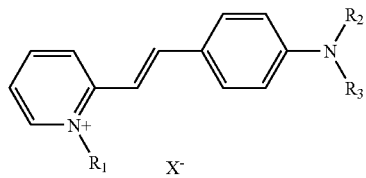

in which:

$R_1$ is a linear or branched alkyl or a cycloalkyl radical, containing 6 to 22 carbon atoms, more particularly 6 to 16 carbon atoms and preferably 8 to 12 carbon atoms, optionally substituted with at least one hydroxyl group, with at least one linear or branched $C_1$-$C_6$ alkoxy or $C_1$-$C_6$ cycloalkoxy group, and/or with at least one cyano group;

$R_2$ and $R_3$, independently of each other, represent a hydrogen atom; a linear or branched alkyl radical containing 1 to 22 carbon atoms, more particularly 1 to 10 and preferably from 1 to 6 carbon atoms, optionally substituted with one or more hydroxyl radicals;

$X^-$ represents an organic or mineral anion.

The fluorescent dye included in the composition according to the invention is more especially a molecule that colours by itself, is soluble in the medium, and absorbs light of the visible spectrum and also possibly of the ultraviolet spectrum (wavelengths ranging from 360 to 760 nm), but which, unlike a standard dye, converts a portion of the absorbed energy into fluorescent light of longer wavelength than that of the absorbed light, emitted in the visible part of the spectrum.

In addition, the fluorescent dye according to the invention is a dye that generates fluorescence on the support onto which it is applied.

According to the present invention, the fluorescent dye is soluble in the medium of the composition to at least 1 g per litre and preferably to at least 5 g per litre at a temperature of 25° C.

When the radical $R_1$ is cycloalkyl or substituted with a cycloalkoxy group, the cyclic portion of the radical is advantageously saturated and preferably 5- to 6-membered, the number of carbon atoms in the ring(s) not being included in the number of carbon atoms of the alkyl or alkoxy chain. Preferably, the cyclic portions are of cyclopentane or cyclohexane type.

More particularly, the radicals $R_2$ and $R_3$ represent a hydrogen atom or a methyl radical.

It should be noted that $X^-$ may be an anion of mineral origin chosen especially from halides, sulfates, bisulfates, nitrates, phosphates, hydrogen phosphates, dihydrogen phosphates, carbonates and bicarbonates.

The anion $X^-$ may also be of organic origin and, in this case, more particularly chosen from anions originating from salts of saturated or unsaturated, aromatic or non-aromatic sulfuric, sulfonic, mono- or polycarboxylic acids, optionally substituted with at least one hydroxyl or amino radical or halogen atoms.

Preferably, $X^-$ is chosen from chloride, iodide, sulfate, methosulfate and ethosulfate.

In accordance with one particularly advantageous embodiment of the invention, the fluorescent compound corresponds to one of the following formulae:

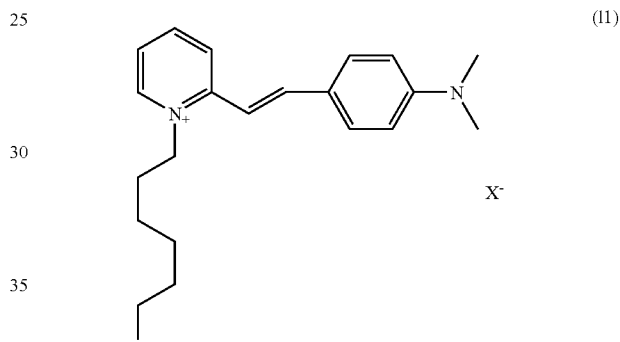

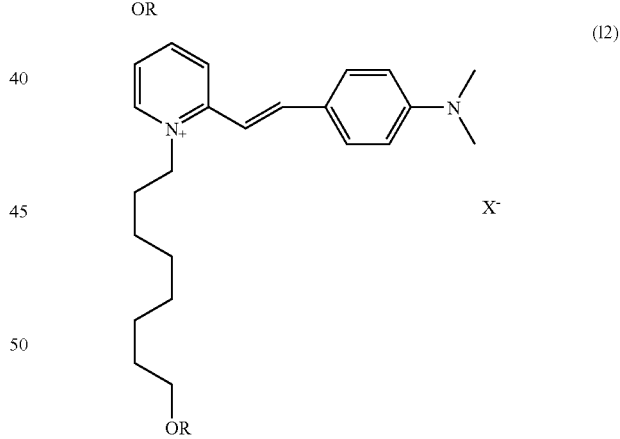

in which formulae R represents a hydrogen atom or a linear or branched $C_1$-$C_4$ alkyl radical and X represents an organic or mineral anion.

The fluorescent dye(s) more particularly represent(s) from 0.01% to 20% and preferably from 0.1% to 5% by weight relative to the total weight of the composition.

The cosmetically acceptable medium generally consists of water or of a mixture of water and of at least one organic solvent.

Examples of organic solvents that may be mentioned include $C_1$-$C_4$ linear or branched alkanols such as ethanol and isopropanol; glycerol; glycols and glycol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, similar products and mixtures thereof.

The solvent(s) may be present in proportions preferably ranging from 1% to 40% by weight approximately and even more preferably from 5% to 30% by weight approximately relative to the total weight of the dye composition.

The pH of the composition in accordance with the invention is generally between 3 and 12 approximately and preferably between 5 and 11 approximately. It may be adjusted to the desired value by means of acidifying or basifying agents usually used in the dyeing of human keratin fibres.

Examples of acidifying agents that may be mentioned include mineral or organic acids, for instance hydrochloric acid, orthophosphoric acid, sulfuric acid, carboxylic acids, for instance acetic acid, tartaric acid, citric acid and lactic acid, and sulfonic acids.

Examples of basifying agents that may be mentioned include aqueous ammonia, alkaline carbonates, alkanolamines such as monoethanolamine, diethanolamine and triethanolamine and derivatives thereof, sodium hydroxide, potassium hydroxide and the compounds of formula (II) below:

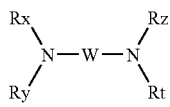

in which W is a propylene residue optionally substituted with a hydroxyl group or a $C_1$-$C_6$ alkyl radical; $R_x$, $R_y$, $R_z$ and $R_t$, which may be identical or different, represent a hydrogen atom or a $C_1$-$C_6$ alkyl or $C_1$-$C_6$ hydroxyalkyl radical.

The cosmetic composition may also comprise one or more additional direct dyes of nonionic, cationic or anionic nature, and preferably cationic or nonionic, or combinations thereof.

Generally, these direct dyes are chosen from nitrobenzene dyes, azo, azomethine, methine, anthraquinone, naphthoquinone, benzoquinone, phenothiazine, indigoid, xanthene, phenanthridine, phthalocyanin, triarylmethane-based dyes and natural dyes, alone or as mixtures.

It may be chosen, for example, from the following red or orange nitrobenzene dyes:

1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chloro-benzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The composition employed in the case of this first variant may also comprise, in addition to or instead of these nitrobenzene dyes, one or more additional direct dyes chosen from yellow, green-yellow, blue or violet nitrobenzene dyes, azo dyes, anthraquinone dyes, naphthoquinone dyes, benzoquinone dyes, indigoid dyes, and triarylmethane-based dyes.

These additional direct dyes may especially be basic dyes, among which mention may be made more particularly of the dyes known in the Color Index, 3rd edition, under the names "Basic Brown 16", "Basic Brown 17", "Basic Yellow 57", "Basic Red 76", "Basic Violet 10", "Basic Blue 26" and "Basic Blue 99", or acidic direct dyes, among which mention may be made more particularly of the dyes known in the Color Index, 3rd edition, under the names "Acid Orange 7", "Acid Orange 24", "Acid Yellow 36", "Acid Red 33", "Acid Red 184", "Acid Black 2", "Acid Violet 43" and "Acid Blue 62", or alternatively cationic direct dyes such as those described in WO 95/01772, WO 95/15144 and EP-A-0 714 954, the content of which forms an integral part of the present invention.

Among the additional yellow and green-yellow nitrobenzene direct dyes that may be mentioned, for example, are the compounds chosen from:

1-β-hydroxyethyloxy-3-methylamino-4-nitrobenzene,
1-methylamino-2-nitro-5-(β,γ-dihydroxypropyl)oxy-benzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethyl-benzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitro-benzene,
1-(β-hydroxyethyl)amino-2-nitrobenzene, and
4-(β-hydroxyethyl)amino-3-nitrobenzamide.

Among the additional blue or violet nitrobenzene direct dyes that may be mentioned, for example, are the compounds chosen from:

1-(β-hydroxyethyl)amino-4-N,N-bis(β-hydroxyethyl)-amino-2-nitrobenzene,
1-(γ-hydroxypropyl)amino-4,N,N-bis(β-hydroxyethyl)-amino-2-nitrobenzene,
1-(β-hydroxyethyl)amino-4-(N-methyl-N-β-hydroxy-ethyl)amino-2-nitrobenzene,
1-(β-hydroxyethyl)amino-4-(N-ethyl-N-β-hydroxyethyl)-amino-2-nitrobenzene,
1-(β,γ-dihydroxypropyl)amino-4-(N-ethyl-N-β-hydroxy-ethyl)amino-2-nitrobenzene,
2-nitro-para-phenylenediamines having the following formula:

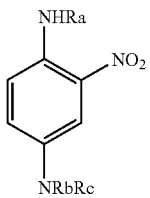

in which:
- R$_b$ represents a C$_1$-C$_4$ alkyl radical or a β-hydroxyethyl, β-hydroxypropyl or γ-hydroxypropyl radical;
- R$_a$ and R$_c$, which may be identical or different, represent a β-hydroxyethyl, β-hydroxypropyl, γ-hydroxypropyl or β,γ-dihydroxypropyl radical, at least one of the radicals R$_b$, R$_c$ or R$_a$ representing a γ-hydroxypropyl radical and R$_b$ and R$_c$ not simultaneously being able to denote a β-hydroxy-ethyl radical when R$_b$ is a γ-hydroxypropyl radical, such as those described in French patent FR 2 692 572.

Among the natural direct dyes that may be mentioned are henna, camomile and indigo, inter alia.

When they are present, the additional direct dye(s) preferably represent(s) from 0.0005% to 12% by weight, and even more preferably from 0.005% to 6% by weight relative to the total weight of the compostion.

When it is intended for oxidation dyeing, the cosmetic composition in accordance with the invention comprises, in addition, at least one oxidation base chosen from the oxidation bases conventionally used for oxidation dyeing and among which mention may be made especially of para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl)amino-2-methylaniline, 4-N,N-bis(β-hydroxyethyl)-amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

Among the para-phenylenediamines mentioned above, the ones most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylamino-ethyloxy-para-phenylenediamine, and the addition salts thereof with an acid or with an alkaline agent.

Among the bis(phenyl)alkylenediamines that may be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxa-octane, and the addition salts thereof with an acid or with an alkaline agent.

Among the para-aminophenols that may be mentioned more particularly, for example, are para-aminophenol, 4-amino-3-methylphenol, 4-amino-3-fluoro-phenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

Among the ortho-aminophenols that may be mentioned more particularly, for example, are 2-aminophenol, 2-amino-5-methylphenol, 2-amino-6-methylphenol and 5-acetamido-2-aminophenol, and the addition salts thereof with an acid or with an alkaline agent.

Among the heterocyclic bases that may be mentioned more particularly, for example, are pyridine derivatives, pyrimidine derivatives and pyrazole derivatives, and the addition salts thereof with an acid or with an alkaline agent.

When they are used, the oxidation base(s) preferably represent(s) from 0.0005% to 12% by weight, and even more preferably from 0.005% to 6% by weight relative to the total weight of the composition.

When it is intended for oxidation dyeing, the composition in accordance with the invention may also comprise at least one coupler so as to modify or to enrich with glints the shades obtained using the fluorescent dyes and the oxidation base(s).

The couplers that may be used may be chosen from the couplers conventionally used in oxidation dyeing, and among which mention may be made especially of meta-phenylenediamines, meta-aminophenols, meta-diphenols and heterocyclic couplers, and the addition salts thereof with an acid or with an alkaline agent.

These couplers are more particularly chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-di-hydroxy-4-methylpyridine, 1H-3-methylpyrazol-5-one, 1-phenyl-3-methylpyrazol-5-one, 2,6-dimethylpyrazolo-[1,5-b]-1,2,4-triazole, 2,6-dimethyl[3,2-c]-1,2,4-triazole and 6-methylpyrazolo[1,5-a]-benzimidazole, and the addition salts thereof with an acid or with an alkaline agent.

When they are present, the coupler(s) preferably represent(s) from 0.0001% to 10% by weight and even more preferably from 0.005% to 5% by weight relative to the total weight of the composition.

In general, the addition salts with an acid that may be used in the context of the compositions of the invention (oxidation bases and couplers) are chosen especially from the hydrochlorides, hydrobromides, sulfates, citrates, succinates, tartrates, tosylates, benzenesulfonates, lactates and acetates.

The addition salts with an alkaline agent that may be used in the context of the compositions of the invention (oxidation bases and couplers) are chosen especially from the addition salts with alkali metals or alkaline-earth metals, with ammonia and with organic amines, including alkanolamines and the compounds of formula (II).

The cosmetic composition in accordance with the invention may also comprise various adjuvants conventionally used in cosmetic compositions, in particular for dyeing human keratin fibres, such as anionic, cationic, nonionic, amphoteric or zwitterionic polymers or mixtures thereof, mineral thickeners, antioxidants, penetrating agents, sequestering agents, fragrances, buffers, dispersants, conditioners, for instance cations, cationic or amphoteric polymers, chitosans, volatile or nonvolatile, modified or unmodified silicones, film-forming agents, ceramides, preserving agents, stabilizers and opacifiers.

The composition may comprise one or more surfactants. These surfactants may be chosen without preference, alone or as mixtures, from anionic, amphoteric, nonionic, zwitterionic and cationic surfactants.

The surfactants that are suitable for carrying out the present invention are especially the following:

(i) Anionic Surfactant(s):

By way of example of anionic surfactants that can be used, alone or as mixtures, in the context of the present invention, mention may be made in particular (non-limiting list) of salts (in particular alkali metal salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; $(C_6-C_{24})$ alkyl sulfosuccinates, $(C_6-C_{24})$alkyl ether sulfosuccinates, $(C_6-C_{24})$alkylamide sulfosuccinates; $(C_6-C_{24})$alkyl sulfoacetates; $(C_6-C_{24})$acyl sarcosinates; and $(C_6-C_{24})$acyl glutamates. It is also possible to use $(C_6-C_{24})$alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates, the alkyl or acyl radical of all of these different compounds preferably containing from 12 to 20 carbon atoms and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated $(C_6-C_{24})$alkyl ether carboxylic acids, polyoxyalkylenated $(C_6-C_{24})$alkylaryl ether carboxylic acids, polyoxyalkylenated $(C_6-C_{24})$alkylamido ether carboxylic acids and their salts, in particular those containing from 2 to 50 alkylene oxide groups, in particular ethylene oxide groups, and mixtures thereof.

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116-178) and their nature is not a critical factor in the context of the present invention. Thus, they can be chosen in particular from (non-limiting list) polyethoxylated or polypropoxylated, alkylphenols, alpha-diols or alcohols, having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as $(C_{10}-C_{14})$ alkylamine oxides or N-acylaminopropylmorpholine oxides.

(iii) Amphoteric or Zwitterionic Surfactant(s):

The amphoteric or zwitterionic surfactants may be chosen especially from aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of $(C_8-C_{20})$alkylbetaines, sulfobetaines, $(C_8-C_{20})$alkylamido$(C_1-C_6)$alkylbetaines or $(C_8-C_{20})$alkylamido$(C_1-C_6)$alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

in which: $R_d$ denotes an alkyl radical of an acid $R_d$—COOH present in hydrolysed coconut oil, a heptyl, nonyl or undecyl radical, $R_e$ denotes a beta-hydroxyethyl group and $R_f$ denotes a carboxymethyl group;

and

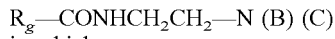

in which:

B represents —CH$_2$CH$_2$OX, C represents —(CH$_2$)$_z$—Y, with z=1 or 2,

X denotes the —CH$_2$CH$_2$—COOH group or a hydrogen atom,

Y denotes —COOH or the —CH$_2$—CHOH—SO$_3$H radical, $R_g$ denotes an alkyl radical of an acid $R_h$—COOH present in coconut oil or in hydrolysed linseed oil, a saturated radical or a radical comprising one or more unsaturations, especially of $C_7$ to $C_{17}$, more particularly a $C_9$, $C_{11}$, $C_{13}$ or $C_{17}$ alkyl radical or its iso form, or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid.

By way of example, mention may be made of the cocoamphodiacetate sold under the trade name Miranol® $C_2M$ concentrate by the company Rhodia Chimie.

(iv) Cationic Surfactants:

Among the cationic surfactants, mention may be made in particular of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

Preferably, the surfactants are nonionic, anionic or amphoteric.

Usually, the surfactants are present in an amount of between 0.01% and 50% by weight and preferably between 0.1% and 25% by weight relative to the total weight of the composition.

The composition may also comprise one or more thickening polymers. These polymers may be ionic or nonionic, and associative or non-associative.

As regards the non-associative thickening polymers, it is first of all recalled that, for the purposes of the present invention, non-associative thickening polymers are thickening polymers not containing a $C_{10}$-$C_{30}$ chain.

Among the non-associative thickening polymers present, mention may be made of crosslinked acrylic acid homopolymers, crosslinked 2-acrylamido-2-methylpropanesulfonic acid homopolymers and the crosslinked acrylamide copolymers thereof, ammonium acrylate homopolymers or copolymers of ammonium acrylate and of acrylamide, nonionic guar gums, biopolysaccharide gums of microbial origin, gums originating from plant exudates, hydroxypropyl- or carboxymethyl celluloses; pectins and alginates, alone or as mixtures.

A first family of suitable non-associative thickening polymers is represented by crosslinked acrylic acid homopolymers.

Among the homopolymers of this type that may be mentioned are those crosslinked with an allylic ether of an alcohol of the sugar series, for instance the products sold under the names Carbopol 980, 981, 954, 2984 and 5984 by the company Noveon, or the products sold under the names Synthalen M and Synthalen K by the company 3 VSA.

The non-associative thickening polymers may also be chosen from crosslinked 2-acrylamido-2-methylpropanesulfonic acid homopolymers and the crosslinked acrylamide copolymers thereof.

As regards these homopolymers and copolymers, which may be partially or totally neutralized, mention may be made of polymers comprising from 90% to 99.9% by weight, relative to the total weight of polymer, of units of formula (j) below:

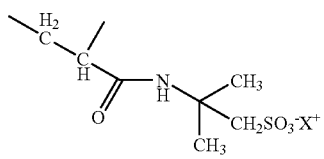

in which $X^+$ denotes a cation or a mixture of cations, or a proton.

More particularly, the cations are chosen from alkali metals (for instance sodium or potassium), ammonium ions optionally substituted with 1 to 3 alkyl radicals, which may be identical or different, containing from 1 to 6 carbon atoms, optionally bearing at least one hydroxyl radical, cations derived from N-methylglucamine or from basic amino acids, for instance arginine and lysine. Preferably, the cation is an ammonium or sodium ion.

Moreover, the polymer comprises from 0.01% to 10% by weight, relative to the total weight of the polymer, of crosslinking units derived from at least one monomer containing at least two ethylenic unsaturations (carbon-carbon double bond).

The crosslinking monomers containing at least two ethylenic unsaturations are chosen, for example, from diallyl ether, triallyl cyanurate, diallyl maleate, allyl(meth)acrylate, dipropylene glycol diallyl ether, polyglycol diallyl ethers, triethylene glycol divinyl ether, hydroquinone diallyl ether, tetraallyloxethanoyl, tetra- or diethylene glycol di(meth)acrylate, triallylamine, tetraallylethylenediamine, trimethylolpropanediallyl ether, trimethylolpropane triacrylate, methylenebis(meth)acrylamide or divinylbenzene, allylic ethers of alcohols of the sugar series, or other allylic or vinyl ethers of polyfunctional alcohols, and also allylic esters of phosphoric and/or vinylphosphonic acid, or mixtures of these compounds.

For further details regarding these polymers, reference may be made to document EP 815 828.

Among the partially or totally neutralized crosslinked copolymers of 2-acrylamido-2-methylpropanesulfonic acid and of acrylamide, mention may be made in particular of the product described in Example 1 of document EP 503 853, and reference may be made to the said document as regards these polymers.

The composition may also comprise, as non-associative thickening polymers, ammonium acrylate homopolymers or copolymers of ammonium acrylate and of acrylamide.

Among the ammonium acrylate homopolymers that may be mentioned is the product sold under the name Microsap PAS 5193 by the company Hoechst. Among the copolymers of ammonium acrylate and of acrylamide that may be mentioned is the product sold under the name Bozepol C Nouveau or the product PAS 5193 sold by the company Hoechst. Reference may be made to documents FR 2 416 723, U.S. Pat. No. 2,798,053 and U.S. Pat. No. 2,923,692 as regards the description and preparation of such compounds.

The composition may also comprise dimethylaminoethyl methacrylate homopolymers quaternized with methyl chloride or dimethylaminoethyl methacrylate copolymers quaternized with methyl chloride and acrylamide.

Among the homopolymers of this type, mention may be made of the products sold under the names Salcare 95 and Salcare 96 by the company Ciba-Allied Colloids. Among the copolymers of this family, mention may be made of the product Salcare $SC_{92}$ sold by Ciba-Allied Colloids or the product PAS 5194 sold by Hoechst. These polymers are especially described and prepared in document EP 395 282, to which reference may be made.

The composition may also comprise nonionic guar gums, for instance the unmodified nonionic guar gums sold under the name Vidogum GH 175 by the company Unipectine and under the name Jaguar C by the company Meyhall.

The nonionic guar gums which may be used according to the invention are preferably modified with $C_1$-$C_6$ hydroxyalkyl groups. Among the hydroxyalkyl groups that may be mentioned, for example, are hydroxymethyl, hydroxyethyl, hydroxypropyl and hydroxybutyl groups.

These guar gums are well known in the prior art and can be prepared, for example, by reacting the corresponding alkene oxides such as, for example, propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhodia Chimie (Meyhall) or under the name Galactasol 4H4FD2 by the company Aqualon.

As examples of suitable non-associative thickening polymers, mention may also be made of biopolysaccharide gums of microbial origin, such as scleroglucan gum or xanthan gum.

Gums derived from plant exudates, such as gum arabic, ghatti gum, karaya gum and gum tragacanth; hydroxypropyl- or carboxymethyl celluloses; pectins and alginates, are also suitable.

These polymers are well known to those skilled in the art and are especially described in Robert L. Davidson's book entitled "Handbook of Water soluble gums and resins" published by the McGraw-Hill Book Company (1980).

Among the thickeners that it is more particularly preferred to use are thickening systems based on associative polymers that are well known to those skilled in the art and especially of nonionic, anionic, cationic or amphoteric nature.

It is recalled that associative polymers are hydrophilic polymers capable, in an aqueous medium, of reversibly associating with each other or with other molecules. Their chemical structure more particularly comprises at least one hydrophilic region and at least one hydrophobic region. The term "hydrophobic group" means a radical or polymer containing a saturated or unsaturated, linear or branched, hydrocarbon-based chain containing at least ten carbon atoms, preferably from 10 to 30 carbon atoms, in particular from 12 to 30 carbon atoms and more preferably from 18 to 30 carbon atoms. Preferably, the hydrocarbon-based group originates from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

The composition may thus comprise at least one associative polymer chosen from associative polyurethanes, which are more particularly cationic or nonionic, associative cellulose derivatives, which are more particularly cationic or nonionic, associative vinyllactams, associative unsaturated polyacids, associative aminoplast-ethers, associative polymers or copolymers comprising at least one ethylenically unsaturated monomer containing a sulfonic group, alone or as mixtures.

Among the associative thickening polymers that may be mentioned are associative polyurethane derivatives, for instance those obtained by polymerization:

about 20% to 70% by weight of an α,β-mono-ethylenically unsaturated carboxylic acid,
about 20% to 80% by weight of a non-surfactant α,β-monoethylenically unsaturated monomer, which is different from the previous monomer,
about 0.5% to 60% by weight of a nonionic monourethane, which is the product of reaction of a monohydroxylated surfactant with a monoethylenically unsaturated monoisocyanate.

Such polymers are especially described in EP 173 109 and more particularly in Example 3. More specifically, this polymer is a methacrylic acid/methyl acrylate/dimethyl meta-isopropenyl benzyl isocyanate terpolymer of ethoxylated behenyl alcohol (40 EO) as an aqueous 25% dispersion. This product is sold under the reference Viscophobe DB1000 by the company Amerchol.

Cationic associative polyurethanes, the family of which has been described in patent application FR 0 009 609, are also suitable for use. It may be represented more particularly by the general formula (A) below:

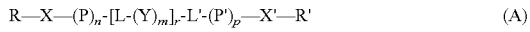

$$R-X-(P)_n-[L-(Y)_m]_r-L'-(P')_p-X'-R' \quad (A)$$

in which:

R and R', which may be identical or different, represent a hydrophobic group or a hydrogen atom;

X and X', which may be identical or different, represent a group comprising an amine function optionally bearing a hydrophobic group, or alternatively a group L";

L, L' and L", which may be identical or different, represent a group derived from a diisocyanate;

P and P', which may be identical or different, represent a group comprising an amine function optionally bearing a hydrophobic group;

Y represents a hydrophilic group;

r is an integer between 1 and 100, preferably between 1 and 50 and in particular between 1 and 25;

n, m and p each range, independently of each other, from 0 to 1000;

the molecule containing at least one protonated or quaternized amine function and at least one hydrophobic group.

In one very advantageous embodiment of these polyurethanes, the only hydrophobic groups are the groups R and R' at the chain ends.

According to one preferred embodiment, the associative polyurethane corresponds to formula (A) in which R and R' both independently represent a hydrophobic group; X and X' each represent a group L"; n and p are between 1 and 1000, and L, L', L", P, P', Y and m have the meaning given as in formula (A).

According to another preferred embodiment of the invention, the associative polyurethane corresponds to formula (A) in which R and R' both independently represent a hydrophobic group, X and X' each represent a group L", n and p are 0, and L, L', L", Y and m have the meaning as in formula (A) indicated previously.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q denotes a leaving group such as a halide, a sulfate, etc.

In accordance with another preferred embodiment of the invention, the associative polyurethane corresponds to formula (A) in which R and R' both independently represent a hydrophobic group; X and X' both independently represent a group comprising a quaternary amine; n and p are zero and L, L', Y and m have the meaning indicated in formula (A).

The number-average molecular mass of the cationic associative polyurethanes is usually between 400 and 500 000, in particular between 1000 and 400 000 and ideally between 1000 and 300 000 g/mol.

When X and/or X' denote(s) a group comprising a tertiary or quaternary amine, X and/or X' may represent one of the following formulae:

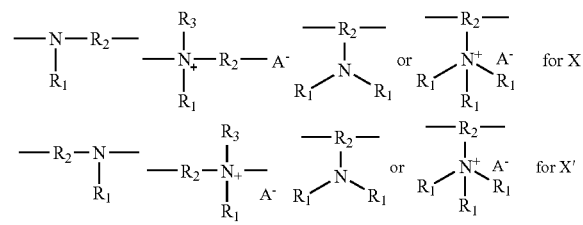

in which:

R$_2$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P;

R$_1$ and R$_3$, which may be identical or different, denote a linear or branched C$_1$-C$_{30}$ alkyl or alkenyl radical or an aryl radical, at least one of the carbon atoms possibly being replaced with a hetero atom chosen from N, S, O and P;

A$^-$ is a physiologically acceptable counterion.

The groups L, L' and L" represent a group of formula:

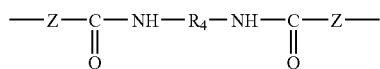

in which:

Z represents —O—, —S— or —NH—; and

R$_4$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P.

The groups P and P' comprising an amine function may represent at least one of the following formulae:

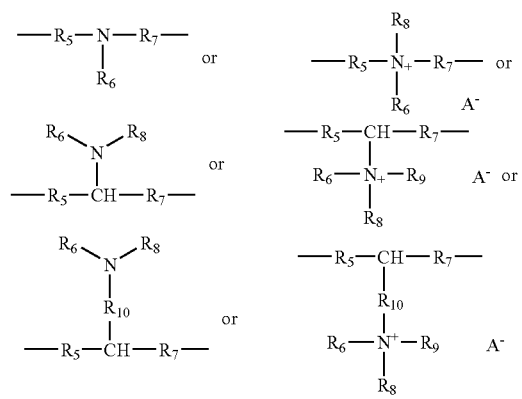

in which:

R$_5$ and R$_7$ have the same meanings as R$_2$ defined above; R$_6$, R$_8$ and R$_9$ have the same meanings as R$_1$ and R$_3$ defined above;

R$_{10}$ represents a linear or branched, optionally unsaturated alkylene group possibly containing one or more hetero atoms chosen from N, O, S and P; and A$^-$ is a cosmetically acceptable counterion.

As regards the meaning of Y, the term "hydrophilic group" means a polymeric or non-polymeric water-soluble group. By way of example, when it is not a polymer, mention may be made of ethylene glycol, diethylene glycol and propylene glycol. When it is a hydrophilic polymer, in accordance with one preferred embodiment, mention may be made, for example, of polyethers, sulfonated polyesters, sulfonated polyamides or a mixture of these polymers. The hydrophilic compound is preferentially a polyether and in particular a poly(ethylene oxide) or poly(propylene oxide).

The associative polyurethanes of formula (A) are formed from diisocyanates and from various compounds with functions containing a labile hydrogen. The functions containing a labile hydrogen may be alcohol, primary or secondary amine or thiol functions, giving, after reaction with the diisocyanate functions, polyurethanes, polyureas and polythioureas, respectively. The expression "polyurethanes which can be used according to the present invention" encompasses these three types of polymer, namely polyurethanes per se, polyureas and polythioureas, and also copolymers thereof.

A first type of compound included in the preparation of the polyurethane of formula (A) is a compound comprising at least one unit containing an amine function. This compound may be multifunctional, but the compound is preferentially difunctional, that is to say that, according to one preferential embodiment, this compound comprises two labile hydrogen atoms borne, for example, by a hydroxyl, primary amine, secondary amine or thiol function. A mixture of multifunctional and difunctional compounds in which the percentage of multifunctional compounds is low may also be used.

As mentioned above, this compound may comprise more than one unit containing an amine function. In this case, it is a polymer bearing a repetition of the unit containing an amine function.

Compounds of this type may be represented by one of the following formulae:

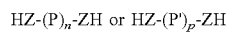

in which Z, P, P', n and p are as defined above.

Examples of compounds containing an amine function that may be mentioned include N-methyldiethanolamine, N-tert-butyldiethanolamine and N-sulfoethyldiethanolamine.

The second compound included in the preparation of the polyurethane of formula (A) is a diisocyanate corresponding to the formula O=C=N—R$_4$—N=C=O, in which R$_4$ is as defined above.

Mention may especially be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound included in the preparation of the polyurethane of formula (A) is a hydrophobic compound intended to form the terminal hydrophobic groups of the polymer of formula (A).

This compound consists of a hydrophobic group and of a function containing a labile hydrogen, for example a hydroxyl, primary or secondary amine, or thiol function.

By way of example, this compound may be a fatty alcohol such as, in particular, stearyl alcohol, dodecyl alcohol or decyl alcohol. When this compound comprises a polymeric chain, it may be, for example, α-hydroxylated hydrogenated polybutadiene.

The hydrophobic group of the polyurethane of formula (A) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, in which R and R' are as defined above and Q denotes a leaving group such as a halide, a sulfate, etc.

The cationic associative polyurethane may also comprise a hydrophilic block. This block is provided by a fourth type of compound involved in the preparation of the polymer. This compound may be multifunctional. It is preferably difunctional. It is also possible to have a mixture in which the percentage of multifunctional compound is low.

The functions containing a labile hydrogen are alcohol, primary or secondary amine or thiol functions. This compound may be a polymer terminated at the chain ends with one of these functions containing a labile hydrogen.

By way of example, when it is not a polymer, mention may be made of ethylene glycol, diethylene glycol and propylene glycol.

When it is a hydrophilic polymer, mention may be made, for example, of polyethers, sulfonated polyesters and sulfonated polyamides, or a mixture of these polymers.

The hydrophilic compound is preferentially a polyether and especially a poly(ethylene oxide) or poly(propylene oxide).

The hydrophilic group termed Y in formula (A) is optional. Specifically, the units containing a quaternary amine or protonated function may suffice to provide the solubility or water-dispersibility required for this type of polymer in an aqueous solution.

Although the presence of a hydrophilic group Y is optional, cationic associative polyurethanes comprising such a group are, however, preferred.

The associative polyurethane derivatives of the invention may also be nonionic polyurethane polyethers. More particularly, the said polymers comprise in their chain both hydrophilic blocks usually of polyoxyethylenated nature, and hydrophobic blocks that may be aliphatic chains alone and/or cycloaliphatic and/or aromatic chains.

Preferably, these polyurethane polyethers comprise at least two hydrocarbon-based lipophilic chains, containing from 6 to 30 carbon atoms, separated by a hydrophilic block, the hydrocarbon-based chains possibly being pendent chains or chains at the end of a hydrophilic block. In particular, it is possible for one or more pendent chains to be provided. In addition, the polymer may comprise a hydrocarbon-based chain at one or both ends of a hydrophilic block.

The polyurethane polyethers may be multiblock, in particular in triblock form. The hydrophobic blocks may be at each end of the chain (for example: triblock copolymer containing a hydrophilic central block) or distributed both at the ends and in the chain (for example multiblock copolymer). These same polymers may also be graft polymers or starburst polymers.

The fatty-chain nonionic polyurethane polyethers may be triblock copolymers whose hydrophilic block is a polyoxyethylenated chain comprising from 50 to 1000 oxyethylenated groups.

The nonionic polyurethane polyethers comprise a urethane bond between the hydrophilic blocks, whence arises the name.

By extension, also featured among the hydrophobic-chain nonionic polyurethane polyethers are those whose hydrophilic blocks are linked to the hydrophobic blocks via other chemical bonds.

As examples of hydrophobic-chain nonionic polyurethane polyethers that may be used in the invention, use may be made of Rheolate® 205 containing a urea function, sold by the company Rheox, or alternatively Rheolates® 208, 204 or 212 or Acrysole® RM 184.

Mention may also be made of the product Elfacos® T210 containing a $C_{12-14}$ alkyl chain and the product Elfacos® T212 containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used described above may also be chosen from those described in the article by G. Fonnum, J. Bakke and Fk. Hansen—Colloid Polym. Sci. 271, 380-389 (1993).

Even more particularly, according to the invention, it is preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol (39%) and water (26%)].

The composition may also comprise polymers derived from associative celluloses, such as:

quaternized cationic celluloses modified with groups comprising at least one hydrophobic chain, such as alkyl, arylalkyl or alkylaryl groups containing at least 8 carbon atoms, or mixtures thereof, quaternized cationic hydroxyethylcelluloses modified with groups comprising at least one hydrophobic chain, such as alkyl, arylalkyl or alkylaryl groups containing at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ hydrophobic chains that may be mentioned include the products Quatrisoft LM 200®, Quatrisoft LM-X 529-18-A®, Quatrisoft LM-X 529-18B® ($C_{12}$ alkyl)

and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.

nonionic cellulose derivatives such as hydroxyethyl celluloses modified with groups comprising at least one hydrophobic chain, such as alkyl, arylalkyl or alkylaryl groups, or mixtures thereof, and in which the alkyl groups are preferably of $C_8$-$C_{22}$, for instance the product Natrosol Plus Grade 330 CS® ($C_{16}$ alkyls) sold by the company Aqualon, or the product Bermocoll EHM 100® sold by the company Berol Nobel, cellulose derivatives modified with polyalkylene glycol alkylphenol ether groups, such as the product Amercell Polymer HM-1500® sold by the company Amerchol.

As regards the associative polyvinyllactams, examples that may be mentioned include the polymers described especially in FR 0 101 106. The said polymers are more particularly cationic polymers and comprise:

a) at least one monomer of vinyllactam or alkylvinyllactam type;
b) at least one monomer of structure (a) or (b) below:

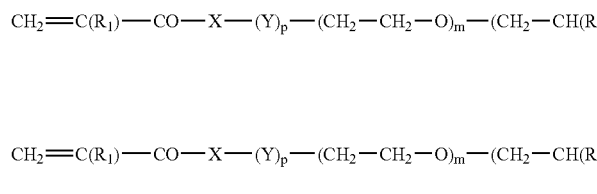

in which:
X denotes an oxygen atom or a radical $NR_6$,
$R_1$ and $R_6$ denote, independently of each other, a hydrogen atom or a linear or branched $C_1$-$C_5$ alkyl radical,
$R_2$ denotes a linear or branched $C_1$-$C_4$ alkyl radical,
$R_3$, $R_4$ and $R_5$ denote, independently of each other, a hydrogen atom, a linear or branched $C_1$-$C_{30}$ alkyl radical or a radical of formula (c):

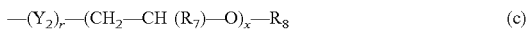

$Y$, $Y_1$ and $Y_2$ denote, independently of each other, a linear or branched $C_2$-$C_{16}$ alkylene radical,
$R_7$ denotes a hydrogen atom, a linear or branched $C_1$-$C_4$ alkyl radical, or a linear or branched $C_1$-$C_4$ hydroxyalkyl radical,
$R_8$ denotes a hydrogen atom or a linear or branched $C_1$-$C_{30}$ alkyl radical,
p, q and r denote, independently of each other, either the value 0 or the value 1,
m and n denote, independently of each other, an integer ranging from 0 to 100,
x denotes an integer ranging from 1 to 100,
Z denotes an organic or mineral acid anion, with the proviso that:
  at least one of the substituents $R_3$, $R_4$, $R_5$ or $R_8$ denotes a linear or branched $C_9$-$C_{30}$ alkyl radical,
  if m or n is other than zero, then q is equal to 1,
  if m or n is equal to zero, then p or q is equal to 0.

The poly(vinyllactam)polymers may be crosslinked or non-crosslinked and may also be block polymers.

Preferably, the counterion $Z^-$ of the monomers of formula (b) is chosen from halide ions, phosphate ions, the methosulfate ion and the tosylate ion.

Preferably, $R_3$, $R_4$ and $R_5$ denote, independently of each other, a hydrogen atom or a linear or branched $C_1$-$C_{30}$ alkyl radical.

More preferably, the monomer b) is a monomer of formula (b) for which, even more preferably, m and n are equal to zero.

The vinyllactam or alkylvinyllactam monomer is preferably a compound of structure (d):

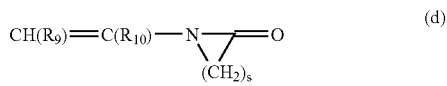

in which:
s denotes an integer ranging from 3 to 6,
$R_9$ denotes a hydrogen atom or a $C_1$-$C_5$ alkyl radical,

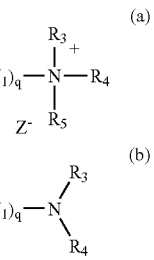

$R_{10}$ denotes a hydrogen atom or a $C_1$-$C_5$ alkyl radical, with the proviso that at least one of the radicals $R_9$ and $R_{10}$ denotes a hydrogen atom.

Even more preferably, the monomer (d) is vinylpyrrolidone.

The poly(vinyllactam)polymers may also contain one or more additional monomers, preferably cationic or nonionic monomers.

As compounds that are more particularly preferred according to the invention, mention may be made of the following terpolymers comprising at least:
a) one monomer of formula (d),
b) one monomer of formula (a) in which p=1, q=0, $R_3$ and $R_4$ denote, independently of each other, a hydrogen atom or a $C_1$-$C_5$ alkyl radical and $R_5$ denotes a $C_9$-$C_{24}$ alkyl radical, and
c) a monomer of formula (b) in which $R_3$ and $R_4$ denote, independently of each other, a hydrogen atom or a $C_1$-$C_5$ alkyl radical.

Even more preferably, terpolymers comprising, by weight, 40% to 95% of monomer (d), 0.1% to 55% of monomer (b) and 0.25% to 50% of monomer (b) will be used. Such polymers are described in particular in patent application WO 00/68282, the content of which forms an integral part of the invention.

As poly(vinyllactam)polymers, vinylpyrrolidone/dimethylaminopropylmethacrylamide/dodecyldimethylmethacrylamidopropylammonium tosylate terpolymers, vinylpyrrolidone/dimethylaminopropylmethacrylamide/cocoyldimethylmethacrylamidopropylammonium tosylate terpolymers, vinylpyrrolidone/dimethylaminopropylmethacrylamide/lauryldimethylmethacrylamidopropylammonium tosylate or chloride terpolymers are used in particular. The vinylpyrrolidone/dimethylaminopropylmethacrylamide/lauryldimethylmethacrylamidopropylammonium chloride terpolymer is sold at a concentration of 20% in water by the company ISP under the name Styleze W20.

The associative polyvinyllactam derivatives of the invention may also be nonionic copolymers of vinylpyrrolidone and of hydrophobic monomers containing a hydrophobic chain, among which mention may be made, for example, of:
the products Antaron V216® or Ganex V216® (vinylpyrrolidone/hexadecene copolymer) sold by the company ISP,
the products Antaron V220® or Ganex V220® (vinylpyrrolidone/eicosene copolymer) sold by the company ISP.

Among the associative unsaturated polyacid derivatives that may be mentioned are those comprising at least one hydrophilic unit of unsaturated olefinic carboxylic acid type, and at least one hydrophobic unit of unsaturated carboxylic acid ($C_{10}$-$C_{30}$) alkyl ester type.

These polymers are especially chosen from those in which the hydrophilic unit of unsaturated olefinic carboxylic acid type corresponds to the monomer of formula (e) below:

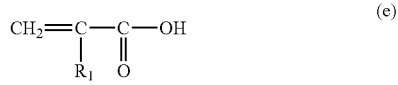

in which $R_1$ denotes H, $CH_3$ or $C_2H_5$, i.e. acrylic acid, methacrylic acid or ethacrylic acid units, and in which the hydrophobic unit of the type ($C_{10}$-$C_{30}$) alkyl ester of an unsaturated carboxylic acid corresponds to the monomer of formula (f) below:

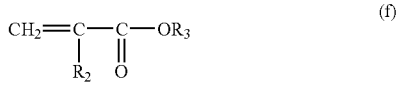

in which formula $R_2$ denotes H or $CH_3$ or $C_2H_5$ (i.e. acrylate, methacrylate or ethacrylate units) and preferably H (acrylate units) or $CH_3$ (methacrylate units), $R_3$ denoting a $C_{10}$-$C_{30}$ and preferably $C_{12}$-$C_{22}$ alkyl radical. ($C_{10}$-$C_{30}$) Alkyl esters of unsaturated carboxylic acids comprise, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate and dodecyl methacrylate.

Anionic polymers of this type are disclosed and prepared, for example, according to U.S. Pat. Nos. 3,915,921 and 4,509,949.

In anionic associative polymers of this type, use is made more particularly of polymers formed from a mixture of monomers comprising:
(i) essentially acrylic acid,
(ii) an ester of formula (f) described above, in which $R_2$ denotes H or $CH_3$, $R_3$ denoting an alkyl radical containing from 12 to 22 carbon atoms, and
(iii) a crosslinking agent, which is a well-known copolymerizable polyethylenic unsaturated monomer, for instance diallyl phthalate, allyl(meth)acrylate, divinylbenzene, (poly)ethylene glycol dimethacrylate or methylenebisacrylamide.

Among the anionic associative polymers of this type, the ones that are preferred are those consisting of from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among the said above polymers, those most particularly preferred are the products sold by the company Goodrich under the trade names Pemulen $TR_1$®, Pemulen $TR_2$® and Carbopol 1382®, and even more preferentially Pemulen $TR_1$®, and the product sold by the company SEPPIC under the name Coatex SX®.

Among the associative unsaturated polyacid derivatives that may also be mentioned are those comprising among their monomers an α,β-monoethylenically unsaturated carboxylic acid and an ester of an α,β-monoethylenically unsaturated carboxylic acid and of an oxyalkylenated fatty alcohol.

These compounds also preferably comprise as monomer an ester of an α,β-monoethylenically unsaturated carboxylic acid and of a $C_1$-$C_4$ alcohol.

An example of compounds of this type that may be mentioned is Aculyn 22® sold by the company Rohm & Haas, which is a methacrylic acid/ethyl acrylate/oxyalkylenated stearyl methacrylate terpolymer.

As regards the thickening polymers of the aminoplast-ether type, any product derived from the condensation of an aldehyde with an amine or an amide, and any structural unit formed from an aminoplast residue and from a divalent hydrocarbon-based residue linked to the aminoplast residue via an ether bond, is designated.

The polymers with an aminoplast-ether skeleton are preferably chosen from those containing at least one unit of structure (g) below:

in which:
AMP is an aminoplast residue with alkylene units (or divalent alkyl),
R denotes a hydrogen atom, a $C_1$-$C_4$ alkyl radical or a $C_1$-$C_4$ acyl radical,
$RO_1$ is a divalent alkyleneoxy residue,
p denotes a positive integer,
the group(s) OR being linked to the alkylene units of the AMP residue.

Preferably, the polymers with an aminoplast-ether skeleton are chosen from those containing at least one unit of structure (h) below:

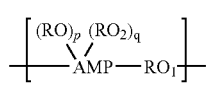
(h)

in which:
AMP, R, RO₁ and p have the same meaning as above,
RO₂ is a group other than RO linked to AMP via a hetero atom and comprising at least two carbon atoms, and
q is a positive integer.

Even more preferably, the polymers correspond to formulae (III) and (IIIa) below:

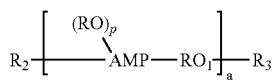
(iii)

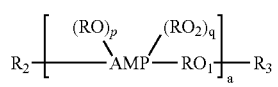
(iiia)

in which:
AMP, R, RO₁, RO₂, p and q have the same meaning as above,
R₂ or R₃, which may be identical or different, represent an end group that can denote a hydrogen atom, a group RO₁H, a group RO₂H, a group AMP(OR)p or any monofunctional group such as alkyl, cycloalkyl, aryl, aralkyl, alkylaryl, alkyloxyalkyl, aryloxyalkyl or cycloalkoxyalkyl,
a being a number greater than 1 and preferably greater than 2.

The aminoplast residues bearing the groups OR thereof integrated into the polymers may be chosen, in a nonlimiting manner, from structures (1) to (12) below:

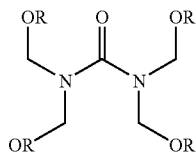
(1)

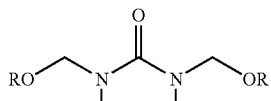
(2)

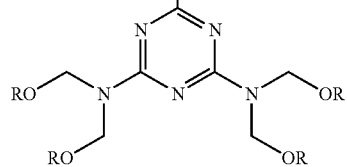
(3)

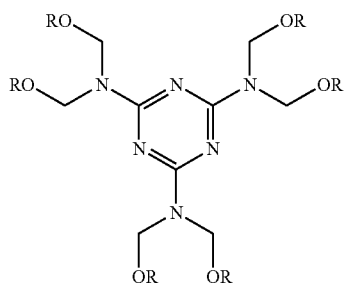
(4)

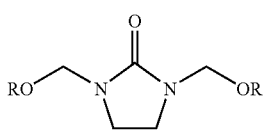
(5)

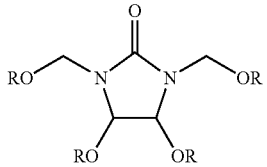
(6)

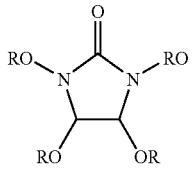
(7)

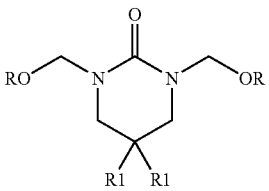
(8)

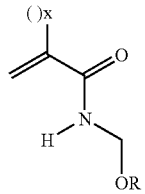
(9)

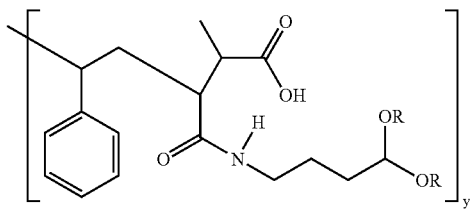
(10)

-continued

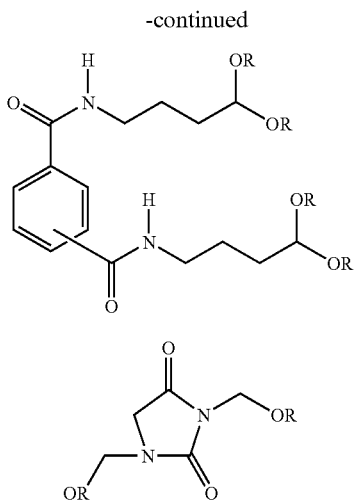

in which:
R has the same meaning as above,
$R_1$ denotes $C_1$-$C_4$ alkyl,
y is a number at least equal to 2,
x denotes 0 or 1.

Preferably, the aminoplast residue(s) bearing the groups OR thereof is (are) chosen from those of structure (13) below:

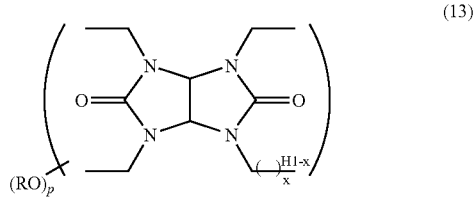

in which R, p and x have the same meanings as above.

The divalent alkyleneoxy residues are preferably those corresponding to the diols of general formula (14) below:

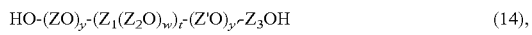

y and y' being numbers ranging from 0 to 1000,
t and w being numbers ranging from 0 to 10,
Z, Z', $Z_2$ and $Z_3$ are $C_2$-$C_4$ alkylene radicals and preferably radicals —$CH_2$—$CH(Z_4)$- and —$CH_2$—$CH(Z_4)$-$CH_2$—, $Z_1$ being a linear or cyclic, branched or unbranched, aromatic or nonaromatic radical optionally comprising one or more hetero atoms and containing from 1 to 40 carbon atoms,
$Z_4$ denoting a hydrogen atom or a $C_1$-$C_4$ alkyl radical or a $C_1$-$C_3$ acyl radical, it being understood that at least one of the radicals $Z_4$ of the radicals Z, Z', $Z_2$ and $Z_3$ is other than an acyl radical.

Preferably, $Z_4$ denotes a hydrogen atom or a methyl radical.

Even more preferably, t=0 and Z, Z' and $Z_3$ denote —$CH_2CH_2$—, and at least one of the groups from among y and y' is other than 0. The compounds of formula (14) are then polyethylene glycols.

The aminoplast-ether polymers of formula (g) are described in particular in patent U.S. Pat. No. 5,914,373, to which reference may be made for further details.

As polymers with an aminoplast-ether skeleton of formula (g), mention may be made in particular of the products Pure-Thix® L [PEG-180/Octoxynol-40/TMMG Copolymer (INCI name)], Pure-Thix M® [PEG-180/Laureth-50/TMMG Copolymer (INCI name)] and Pure-Thix® HH [Polyether-1 (INCI name)]; Pure-Thix TX 1442® [PEG-18/dodoxynol-5/PEG-25 tristyrylphenol/tetramethoxy methyl glycoluril copolymer], sold by the company Süd-Chemie.

The thickening polymers included as ingredient in the composition according to the invention may also be chosen from associative polymers comprising at least one ethylenically unsaturated monomer containing a sulfonic group, in free or partially or totally neutralized form and comprising at least one hydrophobic portion.

Preferably, the said polymers are partially or totally neutralized with a mineral base (sodium hydroxide, potassium hydroxide or aqueous ammonia) or an organic base such as monoethanolamine, diethanolamine, triethanolamine, an aminomethylpropanediol, N-methylglucamine and basic amino acids, for instance arginine and lysine, and mixtures of these compounds.

These associative polymers may or may not be crosslinked, and are preferably crosslinked polymers. In this case, the cross-linking agents are derived from at least one monomer containing at least two ethylenic unsaturations (carbon-carbon double bond).

The crosslinking monomers containing at least two ethylenic unsaturations are chosen, for example, from diallyl ether, triallyl cyanurate, diallyl maleate, allyl(meth)acrylate, dipropylene glycol diallyl ether, polyglycol diallyl ethers, triethylene glycol divinyl ether, hydroquinone diallyl ether, ethylene glycol di(meth)acrylate or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl(meth)acrylate, allylic ethers of alcohols of the sugar series, or other allyl or vinyl ethers of polyfunctional alcohols, and also allylic esters of phosphoric and/or vinylphosphonic acid derivatives, or mixtures of these compounds.

Methylenebisacrylamide, allyl methacrylate or trimethylolpropane triacrylate is used more particularly. The degree of crosslinking generally ranges from 0.01 mol % to 10 mol % relative to the polymer.

The ethylenically unsaturated monomers containing a sulfonic group are chosen especially from vinylsulfonic acid, styrenesulfonic acid, (meth)acrylamido($C_1$-$C_{22}$)alkylsulfonic acids, and N-($C_1$-$C_{22}$)alkyl(meth)acrylamido($C_1$-$C_{22}$)alkylsulfonic acids, for instance undecylacrylamidomethanesulfonic acid, and also partially or totally neutralized forms thereof.

(Meth)acrylamido($C_1$-$C_{22}$)alkylsulfonic acids such as, for example, acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, may be used more particularly.

2-Acrylamido-2-methylpropanesulfonic acid (AMPS), and also partially or totally neutralized forms thereof, are preferably used.

The amphiphilic polymers present in the composition according to the invention may also be chosen from random amphiphilic AMPS polymers modified by reaction with a $C_6$-$C_{22}$ n-monoalkylamine or di-n-alkylamine, and such as those described in patent application WO 00/31154.

The hydrophobic monomers that constitute the hydrophobic portion of the polymer are preferably chosen from the acrylates or acrylamides of formula (k) below:

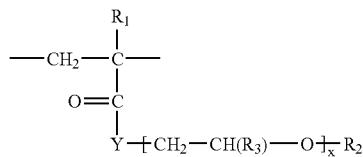

in which $R_1$ and $R_3$, which may be identical or different, denote a hydrogen atom or a linear or branched $C_1$-$C_6$ alkyl radical (preferably methyl); Y denotes O or NH; $R_2$ denotes a hydrophobic hydrocarbon-based radical as defined previously; x denotes a number of moles of alkylene oxide and ranges from 0 to 100.

The radical $R_2$ is advantageously chosen from linear $C_6$-$C_{18}$ alkyl radicals (for example n-hexyl, n-octyl, n-decyl, n-hexadecyl and n-dodecyl) and branched or cyclic $C_6$-$C_{18}$ alkyl radicals (for example cyclododecane ($C_{12}$) or adamantane ($C_{10}$)); $C_6$-$C_{18}$ alkyl-perfluoro radicals (for example the group of formula —$(CH_2)_2$—$(CF_2)_9$—$CF_3$); the cholesteryl radical ($C_{27}$) or a cholesterol ester residue, for instance the cholesteryl oxyhexanoate group; aromatic polycyclic groups, for instance naphthalene or pyrene. Among these radicals, the ones that are more particularly preferred are linear alkyl radicals and more particularly the n-dodecyl radical.

According to one particular form of the invention, the monomer of formula (k) comprises at least one alkylene oxide unit ($x \geq 1$) and preferably a polyoxyalkylenated chain. The polyoxyalkylenated chain preferably consists of ethylene oxide units and/or of propylene oxide units and even more particularly consists of ethylene oxide units. The number of oxyalkylene units generally ranges from 3 to 100, more preferably from 3 to 50 and even more preferably from 7 to 25.

The copolymers may also contain other ethylenically unsaturated hydrophilic monomers, chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in documents EP-A-750 899 and U.S. Pat. No. 5,089,578 and in the following publications from Yotaro Morishima: "Self-assembling amphiphilic polyelectrolytes and their nanostructures—Chinese Journal of Polymer Science Vol. 18, No. 40, (2000), 323-336"; "Micelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694-3704"; "Solution properties of micelle networks formed by nonionic moieties covalently bound to a polyelectrolyte: salt effects on rheological behaviour—Langmuir, 2000, Vol. 16, No. 12, 5324-5332"; "Stimuli responsive amphiphilic copolymers of sodium 2-(acrylamido)-2-methylpropanesulfonate and associative macromonomers—Polym. Preprint, Div. Polym. Chem. 1999, 40(2), 220-221".

The distribution of the monomers in the copolymer may be in random or block form.

Among the polymers of this type, mention may be made more especially of:

crosslinked or non-crosslinked, neutralized or non-neutralized copolymers comprising from 15% to 60% by weight of AMPS units and from 40% to 85% by weight of ($C_8$-$C_{16}$)alkyl(meth)acrylamide units or of ($C_8$-$C_{16}$) alkyl(meth)acrylate units, relative to the polymer, such as those described in patent application EP-A-750 899;

terpolymers comprising from 10 mol % to 90 mol % of acrylamide units, from 0.1 mol % to 10 mol % of AMPS units and from 5 mol % to 80 mol % of n-($C_6$-$C_{18}$)alkyl-acrylamide units, such as those described in U.S. Pat. No. 5,089,578;

copolymers of totally neutralized AMPS and of dodecyl methacrylate, and also crosslinked and non-crosslinked copolymers of AMPS and of n-dodecylmethacrylamide, such as those described in the Morishima articles mentioned above.

Mention will be made more particularly of the copolymers consisting of AMPS units of formula (I) below:

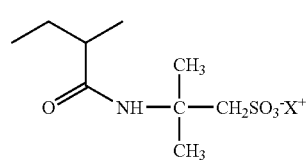

in which $X^+$ has the same definition as previously, and of units of formula (I) below:

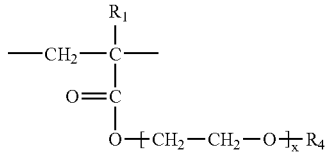

in which x denotes an integer ranging from 3 to 100, preferably from 5 to 80 and more preferably from 7 to 25; $R_1$ has the same meaning as that given above in formula (I) and $R_4$ denotes a linear or branched $C_6$-$C_{22}$ and more preferably $C_{10}$-$C_{22}$ alkyl.

The polymers that are particularly preferred are those for which $x=25$, $R_1$ denotes methyl and $R_4$ represents n-dodecyl; they are described in the Morishima articles mentioned above.

The polymers for which $X^+$ denotes sodium or ammonium are more particularly preferred.

Polymers of the Genapol® range from the company Hoechst/Clariant may be used in the composition according to the invention.

The concentration of associative or non-associative thickening polymer(s) present in the composition according to the invention may range between 0.01% and 10% by weight, more particularly between 0.1% and 5% by weight relative to the weight of the composition, and even more advantageously between 0.5% and 5% by weight relative to the weight of the composition.

Needless to say, a person skilled in the art will take care to select this or these optional additional compound(s) such that the advantageous properties intrinsically associated with the composition in accordance with the invention are not, or are not substantially, adversely affected by the envisaged addition(s).

The composition according to the invention may be in various forms, such as in the form of liquids, shampoos, creams or gels, or in any other suitable form.

One form that is particularly preferred according to the present invention is a dyeing and/or lightening shampoo comprising, in a cosmetically acceptable aqueous medium, at least one fluorescent dye as defined above, and at least one surfactant, which is preferably nonionic.

The nonionic surfactants that are more particularly preferred are chosen from alkylpolyglucosides.

It is not excluded, even if this does not correspond to a preferred embodiment of the invention, for the composition to contain at least one oxidizing agent chosen, for example, from hydrogen peroxide, urea peroxide, alkali metal bromates, persalts such as perborates and persulfates, and enzymes such as peroxidases and two-electron or four-electron oxidoreductases. The use of hydrogen peroxide or of enzymes is particularly preferred.

Another subject of the invention consists of a process for treating keratin fibres and in particular human keratin fibres.

According to a first variant, a composition as defined is applied to the said wet or dry fibres, for a sufficient time, after which the fibres are rinsed, optionally washed with shampoo, rinsed again and dried, or the resulting fibres are left to dry.

According to a second variant of the process, a composition as defined is applied to the said wet or dry fibres without final rinsing.

The first variant may be used for compositions of any type, whether or not they comprise an oxidizing agent and/or a direct dye and/or an oxidation base optionally combined with a coupler.

The second variant is particularly suitable for compositions not comprising an oxidation dye (oxidation base and optionally coupler) or an oxidizing agent.

In the case of the first variant of the process, the application time is usually sufficient to develop the desired coloration and/or lightening.

As a guide, the application time for the composition is from about 5 to 60 minutes and more particularly from about 15 to 60 minutes.

Moreover, the temperature at which the process according to the invention is performed is generally between room temperature (15 to 25° C.) and 60° C. and more particularly between 15 and 45° C.

In the case where the composition comprises an oxidizing agent, the process according to the invention comprises a preliminary step that consists in separately storing, on the one hand, a composition comprising, in a cosmetically acceptable medium, at least one fluorescent dye, optionally at least one direct dye and/or optionally at least one oxidation base optionally combined with at least one coupler, and, on the other hand, a composition comprising, in a cosmetically acceptable medium, at least one oxidizing agent, and then in mixing them together at the time of use. Once this has been performed, the process according to the invention is carried out in accordance with the indications mentioned previously.

Another subject of the invention is a multi-compartment device, comprising at least one compartment containing a composition comprising at least one fluorescent dye, and at least one other compartment containing a composition comprising at least one oxidizing agent. This device may be equipped with a means for applying the desired mixture to the hair, such as the devices described in patent FR-2 586 913.

It should be noted that the in the case where the composition contains at least one additional direct dye and/or at least one oxidation base optionally combined with at least one coupler, according to a first variant, this or these compounds(s) is (are) in the first compartment of the device previously described. According to a second variant, the additional direct dye and/or the oxidation base/coupler are stored in a third compartment.

It should be pointed out that it would not be excluded to have a third variant combining the two previous variants, in which the additional direct dye and/or the oxidation base and optionally the coupler would be partly in the first compartment, with the fluorescent compound, and partly in a third compartment.

The examples that follow are intended to illustrate the invention without, however, limiting its scope.

EXAMPLE 1

The following composition is prepared:

| Fluorescent dye (A) | $1.73 \times 10^{-2}$ mol/l |
|---|---|
| Distilled water | qs 100% |

Compound (A) has the following structure:

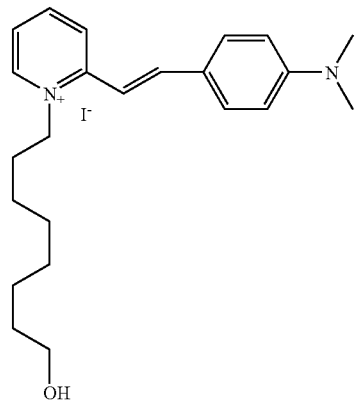

The composition is applied to chestnut-brown hair (tone height of 4) for 20 minutes at room temperature. The bath ratio is set at 5. After dyeing, the locks are rinsed and dried.

A shampoo-fast lightening effect is obtained.

Furthermore, the composition is stable.

EXAMPLE 2

The following composition is prepared:

| Compound (B) | $10^{-3}$ mol % |
|---|---|
| Distilled water | qs 100% |

Compound (B) has the following structure:

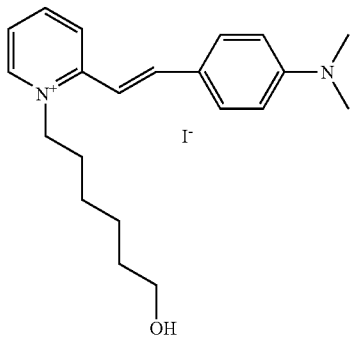

The composition is applied to natural grey hair for 20 minutes at room temperature. The bath ratio is set at 5. After dyeing, the locks are rinsed and dried.

The colour obtained is shampoo-fast.

The composition is stable on storage.

The invention claimed is:

1. A composition comprising:
   a cosmetically acceptable medium wherein said medium is water and optionally at least one organic solvent and at least one fluorescent dye that is soluble in the medium and is comprised in the medium and is chosen from dyes of formula (I) below:

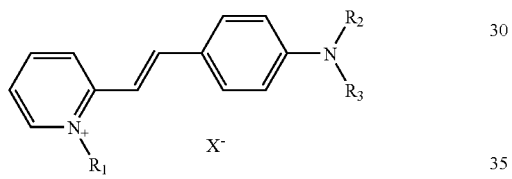

in which:
   $R_1$ is chosen from linear and branched alkyl groups and from cycloalkyl groups, wherein said alkyl and cycloalkyl groups comprise 6 to 22 carbon atoms and are optionally substituted with at least one group chosen from a hydroxyl group, a linear or branched $C_1$-$C_6$ alkoxy group, a linear or branched $C_3$-$C_6$ cycloalkoxy group, and a cyano group;
   $R_2$ and $R_3$, independently of each other, are chosen from a hydrogen atom and from linear and branched alkyl groups comprising 1 to 22 carbon atoms and optionally substituted with at least one hydroxyl group;
   $X^-$ is chosen from an organic anion and a mineral anion.

2. The composition of claim 1, where $R_1$ is chosen from linear and branched alkyl groups having 6 to 16 carbon atoms.

3. The composition of claim 2, where $R_1$ is chosen from linear and branched alkyl groups having 8 to 12 carbon atoms.

4. The composition of claim 1, where $R_1$ is substituted with at least one group chosen from hydroxyl groups, linear or branched $C_1$-$C_6$ alkoxy groups, and cyano groups.

5. The composition of claim 1, where at least one of $R_2$ and $R_3$ is a hydrogen atom.

6. The composition of claim 1, where $R_2$ and $R_3$, independently of each other, are chosen from a hydrogen atom and from linear or branched alkyl groups comprising 1 to 10 carbon atoms optionally substituted with at least one hydroxyl group.

7. The composition of claim 6, where $R_2$ and $R_3$, independently of each other, are chosen from a hydrogen atom and from linear or branched alkyl groups comprising 1 to 6 carbon atoms and optionally substituted with at least one hydroxyl group.

8. The composition of claim 1, where $R_2$ and $R_3$, independently of each other, are chosen from a hydrogen atom and from methyl groups optionally substituted with at least one hydroxyl group.

9. The composition of claim 1, where X is a mineral anion chosen from halides, sulfates, bisulfates, nitrates, phosphates, hydrogen phosphates, dihydrogen phosphates, carbonates and bicarbonates.

10. The composition of claim 1, where X is an organic anion chosen from anions originating from salts of saturated or unsaturated, aromatic or non-aromatic sulfuric, sulfonic, mono- or polycarboxylic acids, optionally substituted with at least one entity chosen from hydroxyl groups, amino groups and halogen atoms.

11. The composition of claim 1, where X is chosen from chloride, iodide, sulfate, methosulfate and ethosulfate.

12. The composition of claim 1, where the at least one fluorescent dye is chosen from compounds of formulas (I1) and (I2):

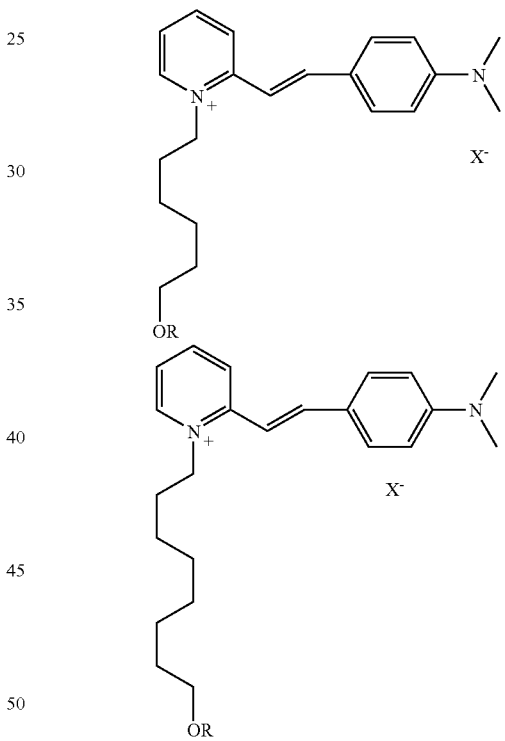

wherein R is chosen from hydrogen and linear or branched $C_1$-$C_4$ alkyl groups, and $X^-$ is chosen from an organic anion and a mineral anion.

13. The composition of claim 1, where the at least one fluorescent dye is present in an amount ranging from 0.01% to 20% by weight relative to the total weight of the composition.

14. The composition of claim 13, where the at least one fluorescent dye is present in an amount ranging from 0.1% to 5% by weight relative to the total weight of the composition.

15. The composition of claim 1, where the composition further comprises at least one additional direct dye chosen from a non-ionic dye, a cationic dye, an anionic dye, and mixtures thereof.

16. The composition of claim 15, where said at least one additional direct dye is chosen from nitrobenzene dyes, azo dyes, anthraquinone dyes, naphthoquinone dyes, benzoquinone dyes, indigoid dyes, triarylmethane-based dyes, natural dyes, and mixtures thereof.

17. The composition of claim 15, where the at least one additional direct dye is present in an amount ranging from 0.0005% to 12% by weight relative to the total weight of the composition.

18. The composition of claim 1, where the composition further comprises at least one surfactant.

19. The composition of claim 18, where the at least one surfactant is chosen from non-ionic surfactants.

20. The composition of claim 18, where the at least one surfactant is present in an amount ranging from 0.01% to 50% by weight relative to the total weight of the composition.

21. The composition of claim 1, where the composition further comprises at least one non-associative thickening polymer.

22. The composition of claim 21, where the at least one non-associative thickening polymer is chosen from crosslinked acrylic acid homopolymers, crosslinked 2-acrylamido-2-methyl propanesulfonic acid homopolymers, and the crosslinked acrylamide copolymers thereof; ammonium acrylate homopolymers; copolymers of ammonium acrylate and of acrylamide; nonionic guar gums; biopolysaccharide gums of microbial origin; gums originating from plant exudates; hydroxypropyl-celluloses; carboxymethyl celluloses; pectins; alginates; and mixtures thereof.

23. The composition of claim 20, where the at least one non-associative thickening polymer is present in an amount ranging from 0.01% to 10% by weight relative to the weight of the composition.

24. The composition of claim 23, where the at least one non-associative thickening polymer is present in an amount ranging from 0.1% to 5% by weight relative to the weight of the composition.

25. The composition of claim 1, where the composition further comprises at least one associative thickening polymer.

26. The composition of claim 25, where the at least one associative thickening polymer is chosen from associative polyurethanes; associative cellulose derivatives; associative vinyllactams; associative unsaturated polyacids; associative aminoplast-ethers; crosslinked 2-acrylamido-2-methylpropanesulfonic acid homopolymers and crosslinked acrylamide copolymers thereof; associative polymers comprising at least one ethylenically unsaturated monomer containing a sulfonic group; copolymers comprising at least one ethylenically unsaturated monomer containing a sulfonic group; and mixtures thereof.

27. The composition of claim 26, wherein said associative polyurethanes are chosen from cationic and nonionic associative polyurethanes.

28. The composition of claim 26, wherein said associative cellulose derivatives are chosen from cationic and nonionic associative cellulose derivatives.

29. The composition of claim 25, where the at least one associative thickening polymer is present in an amount ranging from 0.01% to 10% by weight relative to the weight of the composition.

30. The composition of claim 29, where the amount of at least one associative thickening polymer ranges from 0.1% to 5% by weight relative to the weight of the composition.

31. The composition of claim 1, where the composition in the form of a coloring shampoo.

32. The composition of claim 1, where the composition further comprises at least one oxidation base optionally combined with at least one coupler.

33. The composition of claim 32, where the at least one oxidation base is chosen from para-phenylenediamines, bis-phenyl-alkylene-diamines, para-aminophenols, ortho-aminophenols, heterocyclic bases, and the addition salts thereof with an acid or with an alkaline agent.

34. The composition of claim 32, where the at least one oxidation base is present in an amount ranging from 0.0005% to 12% by weight relative to the total weight of the composition.

35. The composition of claim 32, where the at least one coupler is chosen from meta-phenylenediamines, meta-aminophenols, meta-diphenols, heterocyclic couplers, and the addition salts thereof with an acid or with an alkaline agent.

36. The composition of claim 32, wherein, when present, the at least one coupler is present in an amount ranging from 0.0001% to 10% by weight relative to the total weight of the dye composition.

37. The composition of claim 1, where the composition further comprises at least one oxidizing agent.

38. The composition of claim 37, where the at least one oxidizing agent is chosen from hydrogen peroxide, urea peroxide, alkali metal bromates, persalts, and enzymes, and mixtures thereof.

39. The composition of claim 38, where the persalts are chosen from perborates and persulfates and the enzymes are chosen from peroxidases, two-electron oxidoreductases, and four-electron oxidoreductases.

40. A process for dyeing or lightening keratin fibers comprising:
applying, for a time sufficient to develop a coloration, to said keratin fibers, which can be wet or dry, a composition comprising, in a cosmetically acceptable medium, at least one fluorescent dye that is soluble in the medium, and is chosen from dyes of formula (I) below:

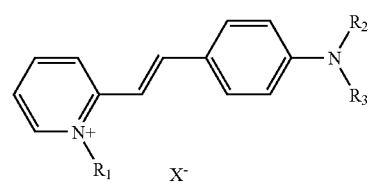

in which:
R$_1$ is chosen from linear and branched alkyl groups and linear and branched cycloalkyl groups, wherein said alkyl groups and cycloalkyl groups comprise 6 to 22 carbon atoms and are optionally substituted with at least one group chosen from a hydroxyl group, linear or branched C$_1$-C$_6$ alkoxy groups, C$_3$-C$_6$ cycloalkoxy groups, and cyano groups;
R$_2$ and R$_3$, independently of each other, are chosen from hydrogen atoms, and from linear or branched alkyl groups comprising 1 to 22 carbon atoms and optionally substituted with at least one hydroxyl group;
X$^-$ is chosen from an organic anion and a mineral anion;
rinsing said fibers;
optionally washing said fibers with shampoo
optionally rinsing the fibers again; and
drying the fibers or leaving the fibers to dry.

41. The process according to claim 40, where the keratin fibers are human keratin fibers.

42. A multi-compartment device for dyeing or lightening keratin fibers, comprising
- at least one compartment comprising a composition comprising, in a cosmetically acceptable medium, at least one fluorescent dye that is soluble in the medium and is chosen from dyes of formula (I) below:

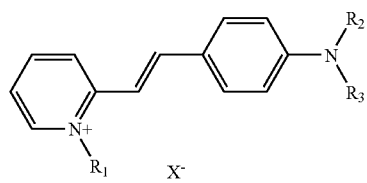

in which:
- $R_1$ is chosen from linear and branched alkyl groups and linear and branched cycloalkyl groups, wherein said alkyl groups and cycloalkyl groups comprise 6 to 22 carbon atoms and are optionally substituted with at least one group chosen from a hydroxyl group, linear or branched $C_1$-$C_6$ alkoxy groups, $C_3$-$C_6$ cycloalkoxy groups, and cyano groups;
- $R_2$ and $R_3$, independently of each other, are chosen from hydrogen atoms, and from linear or branched alkyl groups comprising 1 to 22 carbon atoms and optionally substituted with at least one hydroxyl group;
- $X^-$ is chosen from an organic anion and a mineral anion; and
- at least one other compartment comprising a composition comprising at least one oxidizing agent.

* * * * *

UNITED STATES PATENT AND TRADEMARK OFFICE
CERTIFICATE OF CORRECTION

| | |
|---|---|
| PATENT NO. | : 7,377,946 B2 |
| APPLICATION NO. | : 10/885888 |
| DATED | : May 27, 2008 |
| INVENTOR(S) | : Gourlaouen et al. |

It is certified that error appears in the above-identified patent and that said Letters Patent is hereby corrected as shown below:

In claim 31, column 33, line 66, "composition in" should read --composition is in--.

Signed and Sealed this

Fifth Day of August, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,377,946 B2 | Page 1 of 1 |
| APPLICATION NO. | : 10/885888 | |
| DATED | : May 27, 2008 | |
| INVENTOR(S) | : Gourlaouen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 786 days.

Signed and Sealed this

Fifth Day of October, 2010

David J. Kappos
*Director of the United States Patent and Trademark Office*